United States Patent
Wechter

(10) Patent No.: US 10,406,353 B2
(45) Date of Patent: Sep. 10, 2019

(54) ELECTRICAL STIMULATION LEADS WITH ANCHORING UNIT AND ELECTRODE ARRANGEMENT AND METHODS OF MAKING AND USING

(71) Applicant: BOSTON SCIENTIFIC NEUROMODULATION CORPORATION, Valencia, CA (US)

(72) Inventor: David Ernest Wechter, Santa Clarita, CA (US)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 767 days.

(21) Appl. No.: 14/263,933

(22) Filed: Apr. 28, 2014

(65) Prior Publication Data

US 2014/0343656 A1 Nov. 20, 2014

Related U.S. Application Data

(60) Provisional application No. 61/823,240, filed on May 14, 2013, provisional application No. 61/870,649, filed on Aug. 27, 2013.

(51) Int. Cl.
*A61N 1/05* (2006.01)

(52) U.S. Cl.
CPC ......... *A61N 1/0558* (2013.01); *A61N 1/0551* (2013.01)

(58) Field of Classification Search
CPC .... A61N 1/0558; A61N 1/057; A61N 1/0539; A61N 1/059
See application file for complete search history.

(56) References Cited

U.S. PATENT DOCUMENTS

| 3,754,555 A | 8/1973 | Schmitt |
| 3,814,104 A | 6/1974 | Irnich |

(Continued)

FOREIGN PATENT DOCUMENTS

| WO | 2004028618 | 4/2004 |
| WO | 2005028023 A1 | 3/2005 |

(Continued)

OTHER PUBLICATIONS

Official Communication for U.S. Appl. No. 12/755,756 dated Apr. 16, 2014.

(Continued)

*Primary Examiner* — Tammie K Marlen
(74) *Attorney, Agent, or Firm* — Lowe Graham Jones PLLC; Bruce E. Black

(57) ABSTRACT

An electrical stimulation lead includes a lead body having a distal end portion, a proximal end portion, and a longitudinal length; and electrodes disposed along the distal end portion of the lead body. The electrodes include a first set of electrodes and a second set of electrodes. The electrodes of the first set are spaced apart by a first distance and the electrodes of the second set are spaced apart by a second distance that is greater than the first distance and the first set is spaced apart from the second set by a third distance that is greater than or equal to the second distance. The lead also includes terminals disposed along the proximal end portion of the lead body; conductors electrically coupling the terminals to the electrodes; and anchoring units disposed along the distal end portion of the lead body and proximal to the first set of electrodes.

20 Claims, 7 Drawing Sheets

(56) References Cited

U.S. PATENT DOCUMENTS

| | | |
|---|---|---|
| 4,112,952 A | 9/1978 | Thomas et al. |
| 4,280,512 A | 7/1981 | Karr et al. |
| 4,378,023 A | 3/1983 | Trabucco |
| 4,706,682 A | 11/1987 | Stypulkowski et al. |
| 4,913,147 A | 4/1990 | Fahlstrom et al. |
| 5,052,407 A | 10/1991 | Hauser et al. |
| 5,314,462 A | 5/1994 | Heil, Jr. et al. |
| 5,325,870 A | 7/1994 | Kroll et al. |
| 5,466,255 A | 11/1995 | Franchi |
| 5,492,119 A | 2/1996 | Abrams |
| 5,507,802 A | 4/1996 | Imran |
| 5,571,162 A | 11/1996 | Lin |
| 5,609,623 A | 3/1997 | Lindegren |
| 5,674,273 A | 10/1997 | Helland |
| 5,868,741 A | 2/1999 | Chia et al. |
| 5,871,532 A | 2/1999 | Schroeppel |
| 5,922,014 A | 7/1999 | Warman et al. |
| 5,948,014 A | 9/1999 | Valikai |
| 5,957,966 A | 9/1999 | Schroeppel et al. |
| 6,093,185 A | 7/2000 | Ellis et al. |
| 6,181,969 B1 | 1/2001 | Gord |
| 6,249,708 B1 | 6/2001 | Nelson et al. |
| 6,345,198 B1 | 2/2002 | Mouchawar et al. |
| 6,516,227 B1 | 2/2003 | Meadows et al. |
| 6,609,029 B1 | 8/2003 | Mann et al. |
| 6,609,032 B1 | 8/2003 | Woods et al. |
| 6,671,544 B2 | 12/2003 | Baudino |
| 6,741,892 B1 | 5/2004 | Meadows et al. |
| 6,999,819 B2 | 2/2006 | Swoyer et al. |
| 7,130,700 B2 | 10/2006 | Gardeski et al. |
| 7,187,983 B2 | 3/2007 | Dahlberg et al. |
| 7,244,150 B1 | 7/2007 | Brase et al. |
| 7,328,068 B2 | 2/2008 | Spinelli et al. |
| 7,343,202 B2 | 3/2008 | Mrva et al. |
| 7,369,894 B2 | 5/2008 | Gerber |
| 7,437,193 B2 | 10/2008 | Parramon et al. |
| 7,565,198 B2 | 7/2009 | Bennett et al. |
| 7,672,734 B2 | 3/2010 | Anderson et al. |
| 7,761,165 B1 | 7/2010 | He et al. |
| 7,835,801 B1 | 11/2010 | Sundararajan et al. |
| 7,881,783 B2 | 2/2011 | Bonde et al. |
| 7,899,550 B1 | 3/2011 | Doan et al. |
| 7,927,282 B2 | 4/2011 | Hettrick et al. |
| 7,949,395 B2 | 5/2011 | Kuzma |
| 7,974,706 B2 | 7/2011 | Moffitt et al. |
| 8,096,959 B2 | 1/2012 | Stewart et al. |
| 8,175,710 B2 | 5/2012 | He |
| 8,224,450 B2 | 7/2012 | Brase |
| 8,364,278 B2 | 1/2013 | Pianca et al. |
| 8,452,420 B2 | 5/2013 | Flach et al. |
| 8,469,954 B2 | 6/2013 | Young et al. |
| 8,532,789 B2 | 9/2013 | Smits |
| 2002/0151867 A1 | 10/2002 | McGuckin, Jr. et al. |
| 2002/0156058 A1 | 10/2002 | Borkan |
| 2003/0195600 A1 | 10/2003 | Tronnes et al. |
| 2004/0116992 A1 | 6/2004 | Wardle et al. |
| 2004/0230279 A1 | 11/2004 | Cates et al. |
| 2005/0288722 A1 | 12/2005 | Eigler et al. |
| 2007/0043414 A1 | 2/2007 | Fifer et al. |
| 2007/0049980 A1 | 3/2007 | Zielinski et al. |
| 2007/0150036 A1 | 6/2007 | Anderson |
| 2007/0293923 A1 | 12/2007 | Soltis et al. |
| 2008/0103569 A1 | 5/2008 | Gerber |
| 2008/0103572 A1 | 5/2008 | Gerber |
| 2008/0183253 A1 | 7/2008 | Bly |
| 2008/0183266 A1 | 7/2008 | D'Aquanni et al. |
| 2009/0054949 A1 | 2/2009 | Alexander et al. |
| 2009/0248095 A1 | 10/2009 | Schleicher et al. |
| 2009/0254151 A1 | 10/2009 | Anderson et al. |
| 2010/0168806 A1 | 7/2010 | Norlin-Weissenrieder et al. |
| 2010/0256696 A1 | 10/2010 | Schleicher et al. |
| 2011/0251662 A1 | 10/2011 | Griswald et al. |
| 2012/0053665 A1 | 3/2012 | Stolz et al. |
| 2012/0323253 A1 | 12/2012 | Garai et al. |
| 2013/0066411 A1 | 3/2013 | Thacker et al. |
| 2014/0330287 A1 | 11/2014 | Thompson-Nauman et al. |
| 2015/0039069 A1 | 2/2015 | Rys et al. |
| 2015/0051616 A1 | 2/2015 | Haasl et al. |

FOREIGN PATENT DOCUMENTS

| | | |
|---|---|---|
| WO | 2013082283 | 6/2013 |
| WO | 2015167800 | 11/2015 |

OTHER PUBLICATIONS

Official Communication for U.S. Appl. No. 12/755,756 dated Nov. 27, 2013.

Official Communication for U.S. Appl. No. 12/755,756 dated Jul. 22, 2013.

Official Communication for U.S. Appl. No. 12/755,756 dated Mar. 28, 2013.

Official Communication for U.S. Appl. No. 12/755,756 dated Aug. 16, 2012.

Official Communication for U.S. Appl. No. 12/755,756 dated Apr. 11, 2012.

International Search Report and Written Opinion for PCT/US2014/035753 dated Aug. 7, 2014.

ELECTRICAL STIMULATION LEADS WITH ANCHORING UNIT AND ELECTRODE ARRANGEMENT AND METHODS OF MAKING AND USING

CROSS-REFERENCE TO RELATED APPLICATIONS

This application claims the benefit under 35 U.S.C. § 119(e) of U.S. Provisional Patent Application Ser. No. 61/823,240 filed May 14, 2013 and U.S. Provisional Patent Application Ser. No. 61/870,649 filed Aug. 27, 2013, both of which are incorporated herein by reference.

FIELD

The present invention is directed to the area of implantable electrical stimulation systems and methods of making and using the systems, and in particular implantable electrical stimulation leads having anchoring units interspersed with electrodes and methods of making and using the leads.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

One concern regarding implanted leads is lead migration. This may occur over time and result in movement of the lead away from the desired tissue for stimulation so as to reduce the effectiveness of therapeutic treatment.

BRIEF SUMMARY

One embodiment is an electrical stimulation lead including a lead body having a distal end portion, a proximal end portion, and a longitudinal length; and electrodes disposed along the distal end portion of the lead body. The electrodes include a first set of electrodes and a second set of electrodes. The electrodes of the first set are spaced apart from each other by a first distance and the electrodes of the second set are spaced apart from each other by a second distance that is greater than the first distance and the first set is spaced apart from the second set by a third distance that is greater than or equal to the second distance. The lead also includes terminals disposed along the proximal end portion of the lead body; conductors electrically coupling the terminals to the electrodes; and anchoring units disposed along the distal end portion of the lead body and proximal to all of the electrodes of the first set of electrodes.

Another embodiment is an electrical stimulation lead including a lead body having a distal end portion, a proximal end portion, and a longitudinal length; and electrodes disposed along the distal end portion of the lead body. The electrodes include a first set of electrodes and a second set of electrodes. The electrodes of the first set are spaced apart from each other by a first distance and the electrodes of the second set are spaced apart from each other by a second distance that is greater than the first distance and the first set is spaced apart from the second set by a third distance that is greater than or equal to the second distance. The lead also includes terminals disposed along the proximal end portion of the lead body; conductors electrically coupling the terminals to the electrodes; and anchoring units disposed along the distal end portion of the lead body. The anchoring units include a first set of anchoring units disposed between the first set of electrodes and the second set of electrodes and a second set of anchoring units disposed between the electrodes of the second set of electrodes.

Yet another embodiment is an electrical stimulation system that includes either of the electrical stimulation leads described above and a control module coupleable to the electrical stimulation lead.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems, and in particular implantable electrical stimulation leads having anchoring units interspersed with electrodes and methods of making and using the leads.

Suitable implantable electrical stimulation systems include, but are not limited to, at least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Applications Publication Nos. 2007/0150036 and 2010/0256696, all of which are incorporated by reference.

Figure 1:
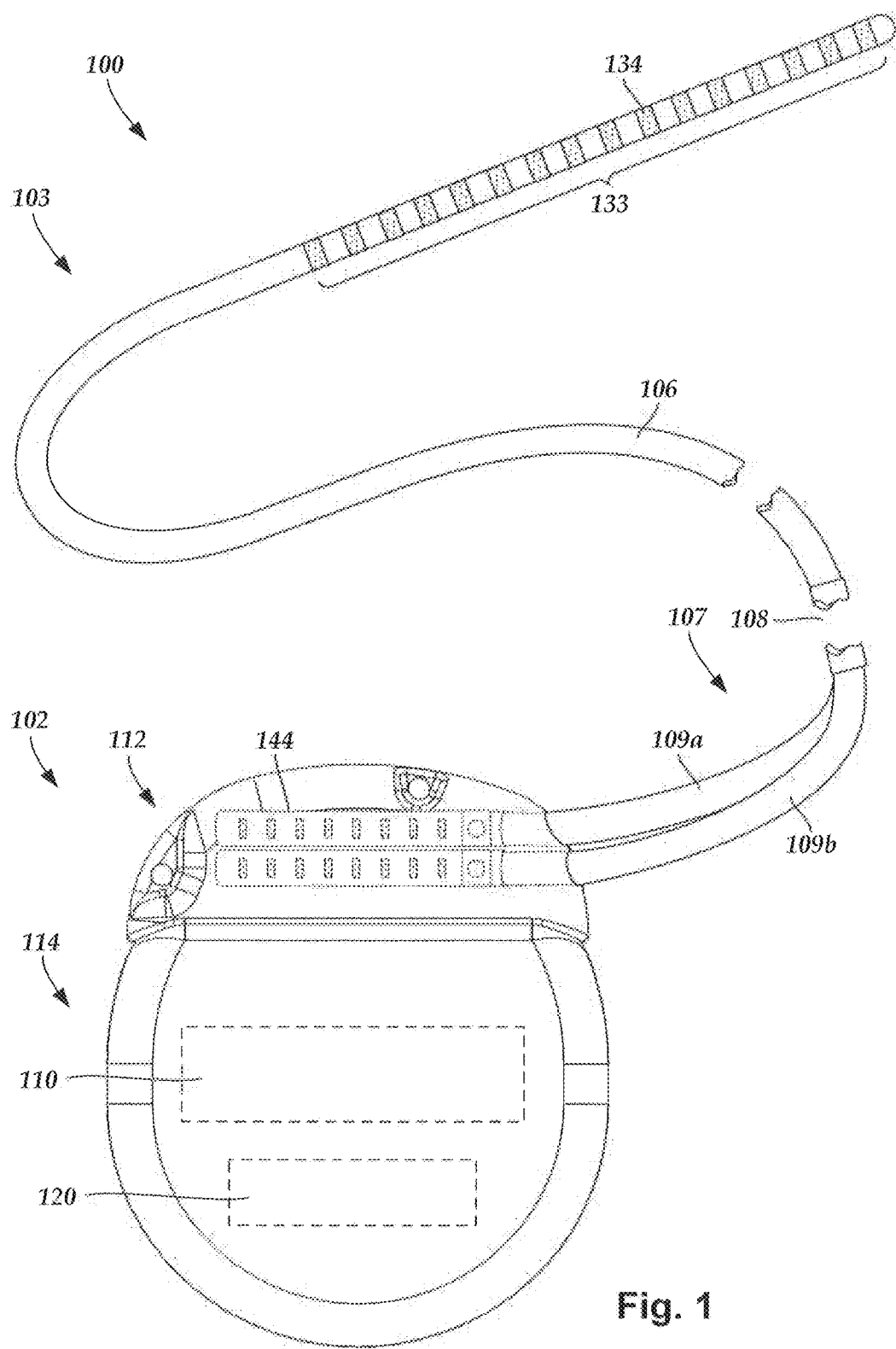
FIG. 1 is a schematic side view of one embodiment of an electrical stimulation system that includes a lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes one or more lead bodies 106, an array of electrodes 133, such as electrode 134, and an array of terminals (e.g., 210 in FIG. 2A-2B) disposed along the one or more lead bodies 106. In at least some embodiments, the lead is isodiametric along a longitudinal length of the lead body 106.

The lead 103 can be coupled to the control module 102 in any suitable manner. In at least some embodiments, the lead 103 couples directly to the control module 102. In at least some other embodiments, the lead 103 couples to the control module 102 via one or more intermediate devices (200 in FIGS. 2A-2B). For example, in at least some embodiments one or more lead extensions 224 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 1, the electrical stimulation system 100 is shown having a splitter 107 configured and arranged for facilitating coupling of the lead 103 to the control module 102. The splitter 107 includes a splitter connector 108 configured to couple to a proximal end of the lead 103, and one or more splitter tails 109a and 109b configured and arranged to couple to the control module 102 (or another splitter, a lead extension, an adaptor, or the like).

The control module 102 typically includes a connector housing 112 and a sealed electronic housing 114. An electronic subassembly 110 and an optional power source 120 are disposed in the electronic housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including one or more of the lead bodies 106 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium. The number of electrodes 134 in each array 133 may vary. For example, there can be two, four, six, eight, ten, twelve, fourteen, sixteen, or more electrodes 134. As will be recognized, other numbers of electrodes 134 may also be used.

The electrodes of the one or more lead bodies 106 are typically disposed in, or separated by, a non-conductive, biocompatible material such as, for example, silicone, polyurethane, polyetheretherketone ("PEEK"), epoxy, and the like or combinations thereof. The lead bodies 105 may be formed in the desired shape by any process including, for example, molding (including injection molding), casting, and the like. The non-conductive material typically extends from the distal end of the one or more lead bodies 106 to the proximal end of each of the one or more lead bodies 106.

Figure 2A:
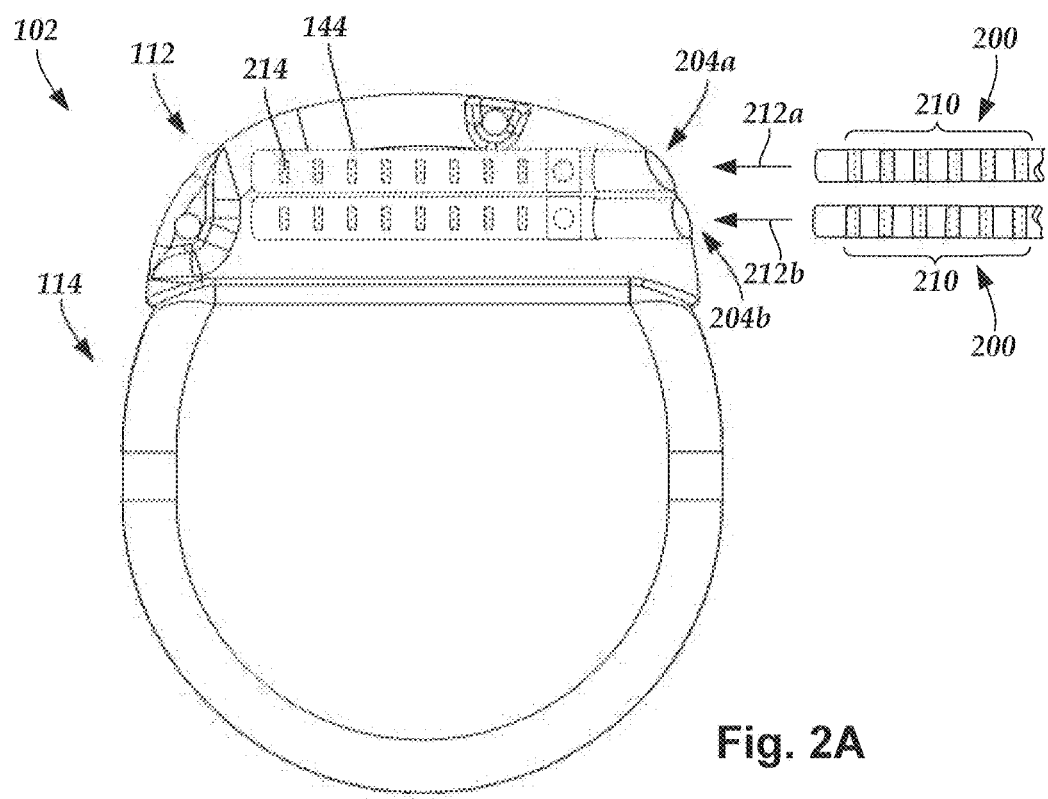
FIG. 2A is a schematic side view of one embodiment of the control module of FIG. 1 configured and arranged to electrically couple to an elongated device, according to the invention.
Figure 2B:
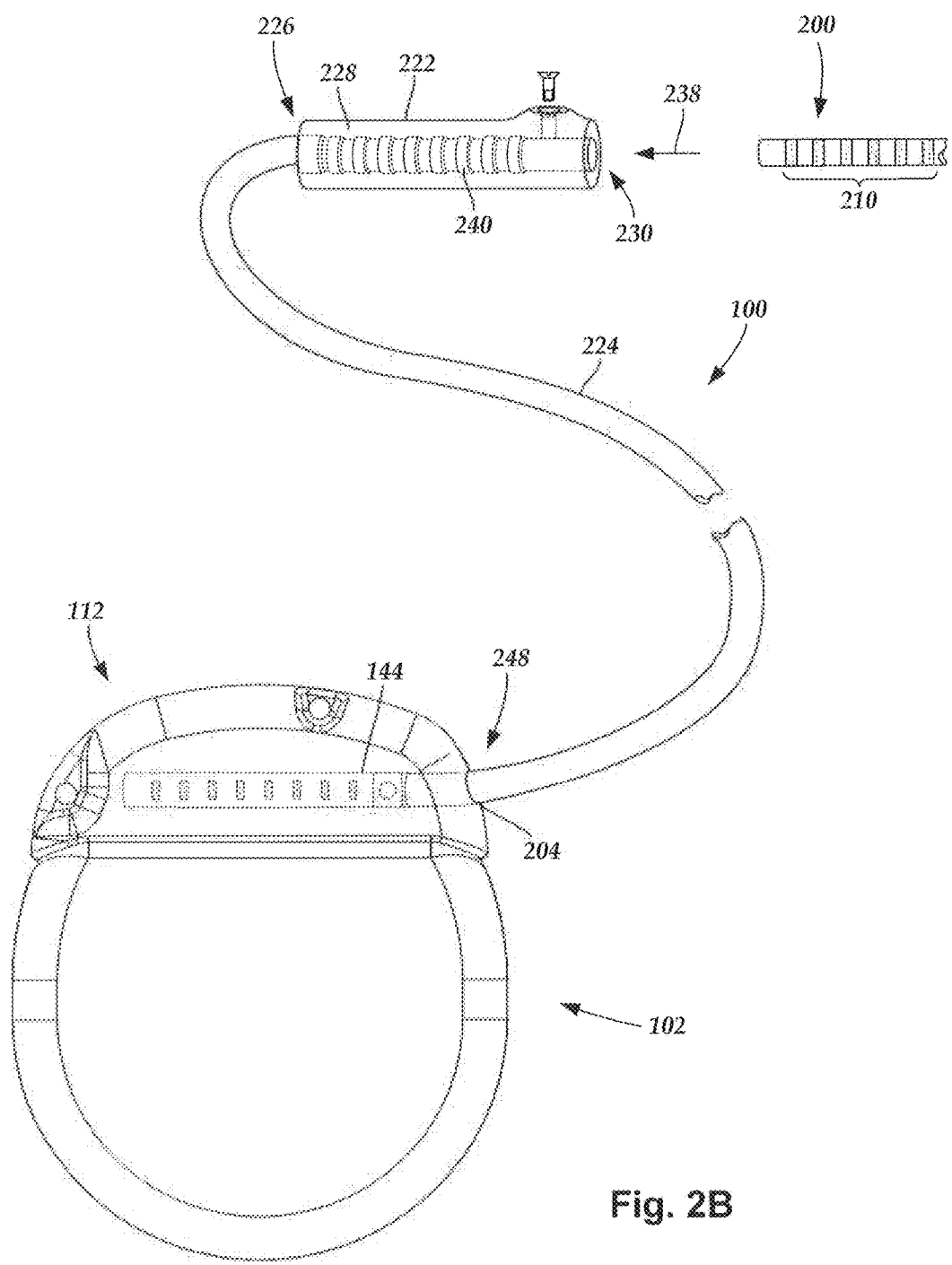
FIG. 2B is a schematic side view of one embodiment of a lead extension configured and arranged to electrically couple the elongated device of FIG. 2A to the control module of FIG. 1, according to the invention.

Terminals (e.g., 210 in FIGS. 2A-2B) are typically disposed along the proximal end of the one or more lead bodies 106 of the electrical stimulation system 100 (as well as any splitters, lead extensions, adaptors, or the like) for electrical connection to corresponding connector contacts (e.g., 214 in FIGS. 2A-2B; and 240 in FIG. 2B). The connector contacts are disposed in connectors (e.g., 144 in FIGS. 1-2B; and 222 in FIG. 2B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the lead body 106, for example, for inserting a stylet to facilitate placement of the lead body 106 within a body of a patient. Additionally, there may be one or more lumens (not shown) that open at, or near, the distal end of the lead body 106, for example for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 2A is a schematic side view of one embodiment of a proximal end of one or more elongated devices 200 configured and arranged for coupling to one embodiment of the control module connector 144. The one or more elongated devices may include, for example, the lead body 106, one or more intermediate devices (e.g., the splitter 107 of FIG. 1, the lead extension 224 of FIG. 2B, an adaptor, or the like or combinations thereof), or a combination thereof.

The control module connector 144 defines at least one port into which a proximal end of the elongated device 200 can be inserted, as shown by directional arrows 212a and 212b. In FIG. 2A (and in other figures), the connector housing 112 is shown having two ports 204a and 204b. The connector housing 112 can define any suitable number of ports including, for example, one, two, three, four, five, six, seven, eight, or more ports.

The control module connector 144 also includes a plurality of connector contacts, such as connector contact 214, disposed within each port 204a and 204b. When the elongated device 200 is inserted into the ports 204a and 204b, the connector contacts 214 can be aligned with a plurality of terminals 210 disposed along the proximal end(s) of the elongated device(s) 200 to electrically coupe the control module 102 to the electrodes (134 of FIG. 1) disposed at a distal end of the lead 103. Examples of connectors in control modules are found in, for example, U.S. Pat. Nos. 7,244,150 and 8,224,450, which are incorporated by reference.

FIG. 2B is a schematic side view of another embodiment of the electrical stimulation system 100. The electrical stimulation system 100 includes a lead extension 224 that is configured and arranged to couple one or more elongated devices 200 (e.g., the lead body 106, the splitter 107, an adaptor, another lead extension, or the like or combinations thereof) to the control module 102. In FIG. 2B, the lead extension 224 is shown coupled to a single port 204 defined in the control module connector 144. Additionally, the lead extension 224 is shown configured and arranged to couple to a single enlongated device 200. In alternate embodiments, the lead extension 224 is configured and arranged to couple to multiple ports 204 defined in the control module connector 144, or to receive multiple elongated devices 200, or both.

A lead extension connector 222 is disposed on the lead extension 224. In FIG. 2B, the lead extension connector 222 is shown disposed at a distal end 226 of the lead extension 224. The lead extension connector 222 includes a connector housing 228. The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 1) disposed along the lead (103 in FIG. 1).

In at least some embodiments, the proximal end of the lead extension 224 is similarly configured and arranged as a proximal end of the lead 103 (or other elongated device 200). The lead extension 224 may include a plurality of electrically conductive wires (not shown) that electrically coupe the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In a least some embodiments, the proximal end 248 of the lead extension 224 is configured and arranged for insertion into a connector disposed in another lead extension (or another intermediate device). In other embodiments (and as shown in FIG. 2B), the proximal end 248 of the lead extension 224 is configured and arranged for insertion into the control module connector 144.

Lead anchoring units can be attached to the lead to facilitate anchoring the lead into patient tissue. The term "tissue" includes, but is not limited to, muscular tissue, connective tissue, organ tissue, bone, cartilage, nerve tissue, and the like. These lead anchoring units, as opposed to conventional lead anchors, can be delivered with the lead through an introducer during the implantation process. The lead anchoring units include anchoring elements that lodge against patient tissue and prevent or reduce lateral or axial (or both lateral and axial) migration of the lead after implantation. The lead anchoring units can be particularly useful for leads for sacral nerve stimulation, spinal cord stimulation, or the stimulation of other patient tissue and organs.

Figure 3:
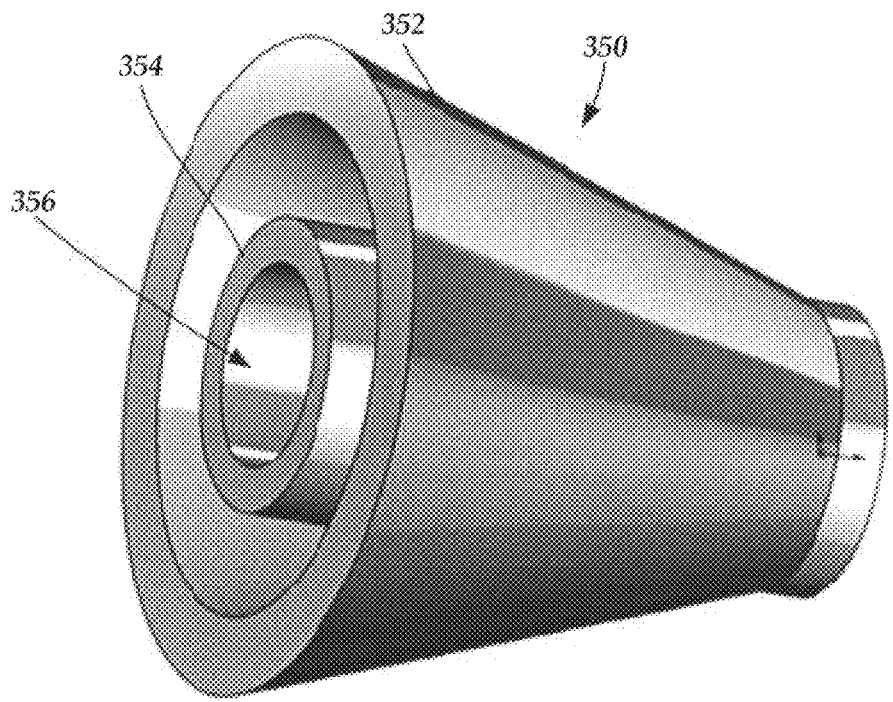
FIG. 3 is a schematic perspective view of one embodiment of a lead anchoring unit, according to the invention.
Figure 6A:
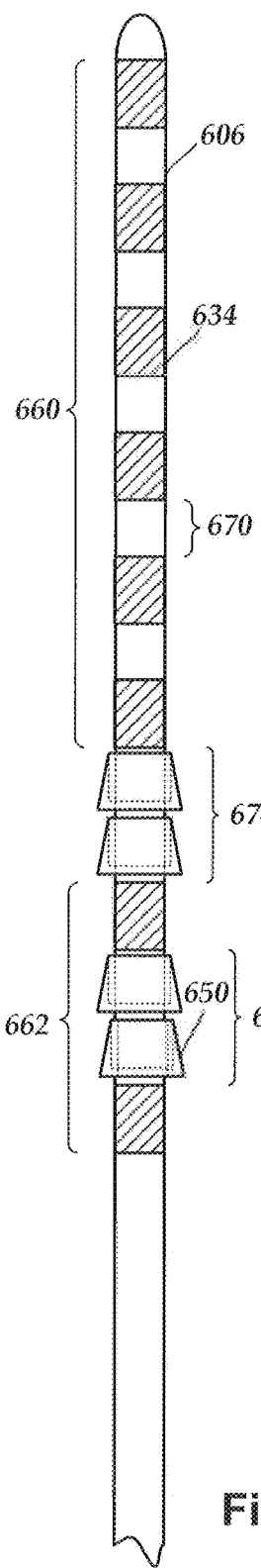
FIG. 6A is a schematic side view of one embodiment of a distal portion of a lead with lead anchoring units disposed thereon, according to the invention.

FIG. 3 is a schematic perspective view of one embodiment of a lead anchoring unit 350 that will be disposed along a distal end portion of a lead body (e.g., the lead body 106 as shown in FIG. 1 or the lead body 606 of FIG. 6A). The lead anchoring unit facilitates anchoring the lead body to the surrounding tissue when implanted within a patient's body.

The anchoring unit 350 includes a lead attachment element 354 having a tube-shaped (e.g., cylindrical) configuration. As shown, the lead attachment element 354 has a proximal end 351, a distal end 353, and a central lumen 356 extending between the two ends 351, 353. The central lumen 356 may be referred to as an "attachment lumen 356". The attachment lumen 356 is employed to receive at least a portion of the lead body of a lead. In at least some embodiments, the lead attachment element 354 has a circular cross-section. However, the lead attachment element 354 can be formed of any other suitable shape, including shapes having an elliptical, rectangular, polygonal, irregular, or any other suitable lateral cross-section. The lead attachment element 354 can have a uniform lateral cross-section along its entire length or a varying lateral cross-section along its length. In at least some embodiments, the cross-section and dimensions of the lead attachment element 354 are dictated by the configuration of the lead body. In at least some embodiments, the outer diameter of the lead body may be slightly larger than the diameter of the attachment lumen 356 so that the lead attachment element fits snuggly on the lead body.

The anchoring unit 350 includes at least one anchoring element 352 coupled to the lead attachment element 354. Although the coupling may occur anywhere along the lead attachment element 354, in the illustrated embodiment, the anchoring element is coupled to the lead attachment element at, or immediately adjacent to, its distal end 353.

In the illustrated embodiment, the anchoring element 352 includes a cone that extends over the lead attachment element 354. In at least some embodiments, the cone is longer than the lead attachment element 354 so that the cone extends over, and beyond, the lead attachment element 354. In other embodiments, the cone may be shorter than the lead attachment element and only extend over a portion the lead attachment element. The anchoring element 352 may have any other suitable shape to interact with patient tissue to anchor the lead to the tissue.

In at least some embodiments, an interior surface 355 of the lead attachment element 354 may be patterned to assist in maintaining the position of the lead anchoring unit on the lead. The pattern may be regular or irregular and may include features, such as, but not limited to, surface roughening, cutouts, grooves, regular or irregular shapes, or the like. In at least some embodiments, an outer surface of the lead body 106 may be patterned. The pattern may be regular or irregular and may include features, such as, but not limited to, surface roughening, cutouts, grooves, regular or irregular shapes, or the like. In some embodiments, both the interior surface of the lead attachment element and the outer surface of the lead body are patterned. The patterning of the lead attachment element and the lead body may be complementary. In at least some embodiments, the pattern on the interior surface of the lead attachment element and the pattern on the exterior surface of the lead body can be generated so that the two patterns interlock with each other.

The patterning described above may be formed using any suitable method, including, but not limited to, ablation (e.g., RF or laser ablation), grinding, knurling, chemical etching, or the like. The patterning may be made on the spacers (i.e., between adjacent or consecutive electrodes) of the lead body 106.

The anchoring unit 350 may form a friction fit with the lead body to hold the anchoring unit in place. Additionally and alternatively, an adhesive, such as a silicone adhesive, may be employed to bond the anchoring unit 350 to the lead body.

The anchoring unit 350 may be formed of any suitable material, such as any suitable biocompatible material including, but not limited to, metals, polymers, alloys, or the like. In at least some embodiments, the anchoring unit 350 is formed of silicone, polyurethane, or the like. In some embodiments, the material that is used has a stiffness that is sufficient to anchor the lead body to the surrounding tissue, while also having sufficient flexibility to reduce, or in some cases avoid, damage or injury to the tissue or to facilitate delivery of the lead with the anchoring unit(s) through an introducer.

In particular, the anchoring unit 350 may be configured to facilitate deployment through an introducer, such as a needle or cannula. In at least some embodiments, the anchoring unit 350 is sufficiently pliable so that it can be compressed within an introducer during implantation. When the introducer is removed, the anchoring unit 350 may then expand to anchor the lead body 106 to the tissue.

Figure 4:
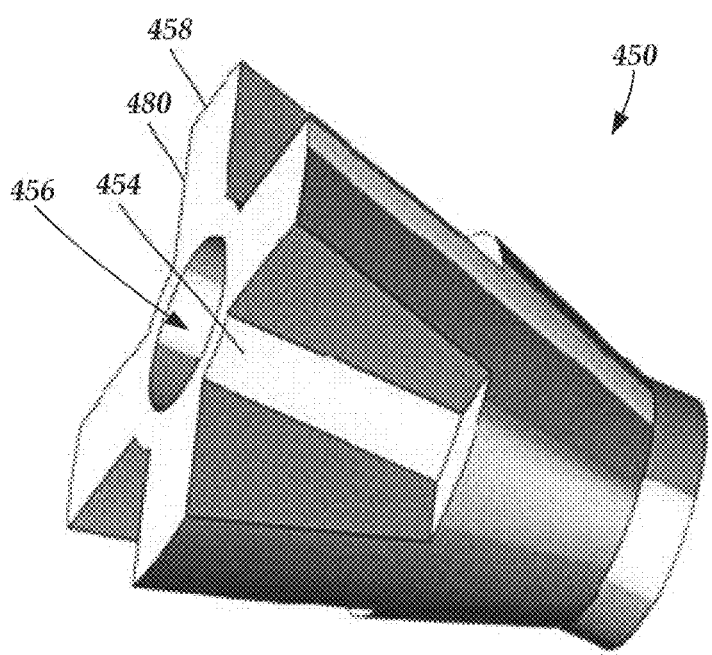
FIG. 4 is a schematic perspective view of a second embodiment of a lead anchoring unit, according to the invention.

FIG. 4 illustrates a second embodiment of a lead anchoring unit 450 that includes a lead attachment element 454 and at least one anchoring element 458. The lead attachment element 454 receives and attaches to a portion of a lead body 106. The at least one anchoring element 458 anchor the lead body to the patient's tissue.

The lead attachment element 454 has a tube-shaped (e.g., cylindrical) configuration, and includes a proximal end 451, a distal end 453, and a central lumen 456 extending therebetween. The central lumen may also be referred to as "attachment lumen 456". In at least some embodiments, the lead attachment element 454 has a circular lateral cross-section. However, the lead attachment element 454 can be formed of any other suitable shape, including shapes having an elliptical, rectangular, polygonal, irregular, or any other suitable cross-section. The lead attachment element 454 can have a uniform lateral cross-section along its entire length or a varying lateral cross-section along its length. In at least some embodiments, the cross-section and dimensions of the lead attachment element 454 are dictated by the configuration of the lead body. In at least some embodiments, the outer diameter of the lead body may be slightly larger than the diameter of the attachment lumen 456.

In at least some embodiments, an interior surface 455 of the lead attachment element 454 may be patterned to assist is maintaining the position of the lead anchoring unit on the lead. The pattern may be regular or irregular and may include features, such as, but not limited to, surface roughening, cutouts, grooves, regular or irregular shapes, or the like. In at least some embodiments, an outer surface of the lead body 106 may be patterned. The pattern may be regular or irregular and may include features, such as, but not limited to, surface roughening, cutouts, grooves, regular or irregular shapes, or the like. In some embodiment, both the interior surface of the lead attachment element and the outer surface of the lead body are patterned. The patterning of the lead attachment element and the lead body may be complementary. In at least some embodiments, the pattern on the interior surface of the lead attachment element and the pattern on the exterior surface of the lead body can be generated so that the two patterns interlock with each other.

The patterning described above may be formed using any suitable method, including, but not limited to, ablation (e.g., RF or laser ablation), grinding, knurling, chemical etching, or the like. The patterning may be made on the spacers (i.e., between adjacent or consecutive electrodes) of the lead body 106.

The anchoring unit 450 may form a friction fit with the lead body to hold the anchoring unit in place. Additionally and alternatively, an adhesive, such as a silicone adhesive, may be employed to bond the anchoring unit 350 to the lead body.

The anchoring element(s) 458 are disposed around the lead attachment element 454 and extend away from the lead attachment element 454. In the illustrated embodiment, the anchoring elements 458 are fins. Any number of fins (or other attachment elements) can be used. The embodiment shown in FIG. 4 includes four fins 480 disposed about the circumference of the lead attachment element 454. The fins 480 shown in FIG. 4 have a trapezoid-shaped configuration, but it will be recognized that the fins 480 can have any suitable shape including, but not limited to, triangular, rectangular, irregular, and the like. Any suitable number of fins may be disposed about the circumference of the lead attachment element 454 including, but not limited to, two, three, four, five, six, seven, eight, or more fins. The fins can be spaced apart uniformly or non-uniformly around the circumference of the lead attachment element 454. In some embodiments, the fins 480 form an angle of ninety degrees with the lead attachment element as illustrated in FIG. 4, but it will be recognized that the fins could extend at a different angle from the lead attachment element (for example, an angle in the range from 30 to 85 degrees).

The fins 480 are shown in FIG. 4 as extending along a partial length of the lead attachment element 454, while being disposed about the circumference of the lead attachment element 454. However, in some other embodiments, such as the embodiment shown in FIG. 5, the fins 480 can extend along an entire length of the lead attachment element 454.

Figure 5:
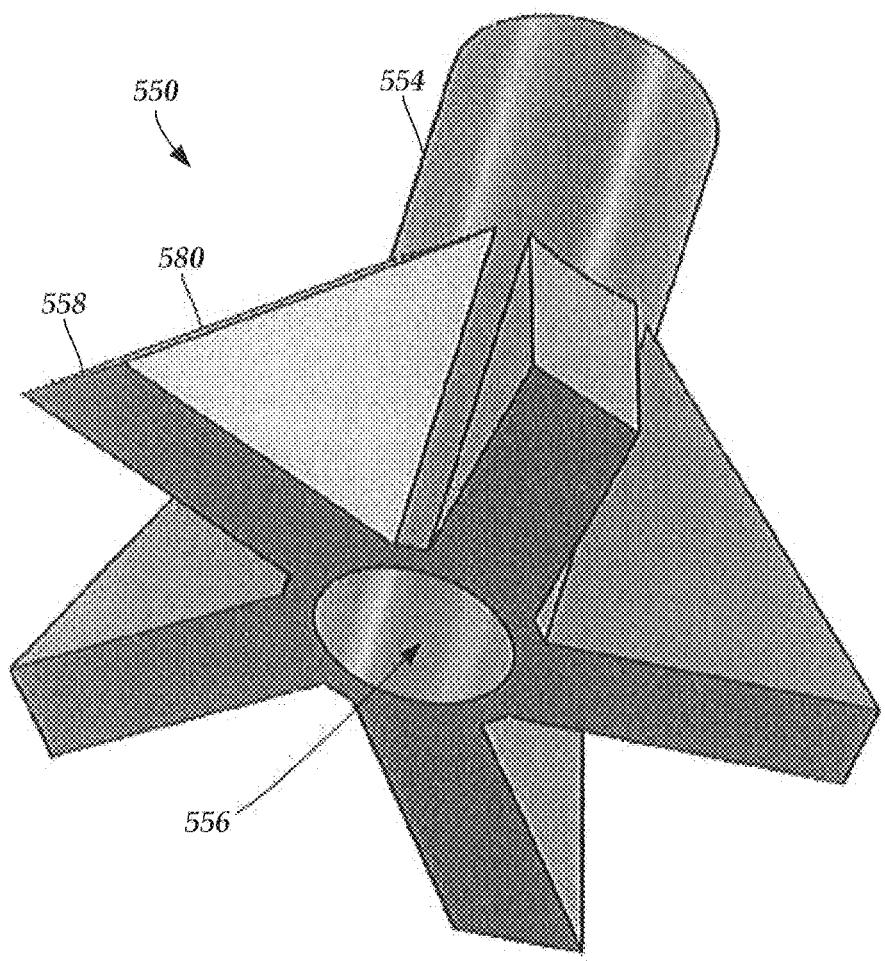
FIG. 5 is a schematic perspective view of the third embodiment of a lead anchoring unit, according to the invention.

FIG. 5 illustrates a third embodiment of a lead anchoring unit 550 that includes a lead attachment element 554 and at least one anchoring element 558. The lead attachment element 554 receives and attaches to a portion of a lead body 106. The at least one anchoring element 558 anchor the lead body to the patient's tissue.

The lead attachment element 554 has a tube-shaped (e.g., cylindrical) configuration, and includes a proximal end 551, a distal end 553, and a central lumen 556 extending therebetween. The central lumen may also be referred to as "attachment lumen 556". In at least some embodiments, the lead attachment element 554 has a circular lateral cross-section. However, the lead attachment element 554 can be formed of any other suitable shape, including shapes having an elliptical, rectangular, polygonal, irregular, or any other suitable cross-section. The lead attachment element 554 can have a uniform lateral cross-section along its entire length or a varying lateral cross-section along its length. In at least some embodiments, the cross-section and dimensions of the lead attachment element 554 are dictated by the configuration of the lead body. In at least some embodiments, the outer diameter of the lead body may be slightly larger than the diameter of the attachment lumen 556.

In at least some embodiments, an interior surface 555 of the lead attachment element 554 may be patterned to assist in maintaining the position of the lead anchoring unit on the lead. The pattern may be regular or irregular and may include features, such as, but not limited to, surface roughening, cutouts, grooves, regular or irregular shapes, or the like. In at least some embodiments, an outer surface of the lead body 106 may be patterned. The pattern may be regular or irregular and may include features, such as, but not limited to, surface roughening, cutouts, grooves, regular or irregular shapes, or the like. In some embodiments, both the interior surface of the lead attachment element and the outer surface of the lead body are patterned. The patterning of the lead attachment element and the lead body may be complementary. In at least some embodiments, the pattern on the interior surface of the lead attachment element and the pattern on the exterior surface of the lead body can be generated so that the two patterns interlock with each other.

The patterning described above may be formed using any suitable method, including, but not limited to, ablation (e.g., RF or laser ablation), grinding, knurling, chemical etching, or the like. The patterning may be made on the spacers (i.e., between adjacent or consecutive electrodes) of the lead body 106.

The anchoring unit 550 may form a friction fit with the lead body to hold the anchoring unit in place. Additionally and alternatively, an adhesive, such as a silicone adhesive, may be employed to bond the anchoring unit 350 to the lead body.

The anchoring element(s) 558 are disposed around the lead attachment element 554 and extend away from the lead attachment element 554. In the illustrated embodiment, the anchoring elements 558 are fins. Any number of fins (or other attachment elements) can be used. The embodiment show in FIG. 5 includes five fins 580 disposed about the circumference of the lead attachment element 554. The fins 580 shown in FIG. 5 have a triangular-shaped configuration, but it will be recognized that the fins 580 can have any suitable shape including, but not limited to, trapezoidal, rectangular, irregular, and the like. Any suitable number of fins may be disposed about the circumference of the lead attachment element 554 including, but not limited to, two, three, four, five, six, seven, eight, or more fins. The fins can be spaced apart uniformly or non-uniformly around the circumference of the lead attachment element 554. In some embodiments, the fins 580 form and angle of ninety degrees with the lead attachment element as illustrated in FIG. 5, but it will be recognized that the fins could extend at a different angle from the lead attachment element (for example, an angle in the range from 30 to 85 degrees).

The fins 580 are shown in FIG. 5 as extending along a partial length of the lead attachment element 554, while being disposed about the circumference of the lead attachment element 554. However, in some other embodiments, such as the embodiment shown in FIG. 5, the fins 580 can extend along an entire length of the lead attachment element 554.

The anchoring units illustrated in FIGS. 3-5 and described above can be useful in anchoring a lead within patient tissue. Examples of other suitable anchoring units can be found in U.S. Patent Application Publication No. 2010/0256696, incorporated herein by reference. When anchoring a lead within tissue, the specific site of placement of the anchoring units within the tissue can also enhance anchoring. For example, if the lead is to be used to stimulate the sacral nerve and the lead is implanted through the sacral foramen, it may be useful to position at some of the anchoring units on the lead so that they will engage the sacral foramen or tissue (such as the fascia) around the sacral foramen, or any combination thereof. To do so, these anchoring units should be placed at suitable locations along the lead. Stimulation of the sacral nerve can be useful to treat overactive bladder, urinary or fecal incontinence, and the like and other diseases or dysfunctions.

Moreover, it has been found that placement of an electrode proximal to the anchoring unit may mechanically stabilize the anchoring unit to prevent or reduce dislodgement or sliding of the anchoring unit from its position on the lead. The electrode may also enhance the anchoring effect of the anchoring unit. Furthermore, placement of electrodes near the anchoring units facilitates identification of the site of the anchoring units by fluoroscopy or similar techniques. The electrodes stand out on fluoroscopic images, whereas the anchoring units are often made of material similar to the lead body and are often more difficult to identify on fluoroscopic images.

Figure 6B:
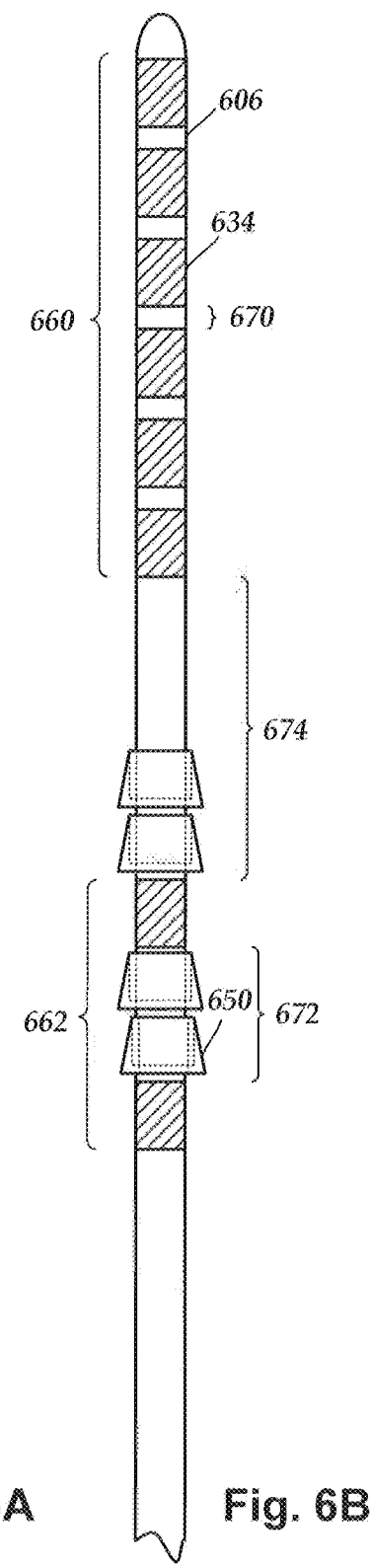
FIG. 6B is a schematic side view of another embodiment of a distal portion of a lead with lead anchoring units disposed thereon, according to the invention.

To provide electrodes proximal to the anchoring units will result in modifying the placement of electrodes as compared to conventional leads. FIGS. 6A and 6B illustrate two embodiments of leads with anchoring units and two different sets of electrodes that are arranged for stimulation and for placement with respect to the anchoring units. FIGS. 6A and 6B each illustrate a distal portion of a lead body 606, with lead anchoring units 650 disposed thereon. The electrode arrangements are different between the two embodiments of FIGS. 6A and 6B.

The distal portion of the lead body 606 includes multiple spaced apart electrodes 634. The electrodes 634 are disposed in two distinct sets: a first set 660 and a second set 662. The first set 660 of electrodes is, at least in some embodiments, distal to all of the anchoring units 650 and is primarily positioned to stimulate patient tissue.

The electrodes of the second set 662 are spaced apart from the first set 660 and are each proximal to one or more of the anchoring units 650. In at least some embodiments, the electrodes of the second set 662 may stabilize or enhance the effect the anchoring units or assist in identification of the site of the anchoring units on fluoroscopic images. In at least some embodiments, one or more of the electrodes of the second set 662 are also positioned to stimulate patient tissue. In at least some embodiments, at least one of the electrodes of the second set 662 is positioned proximal to all of the anchoring units 650, as illustrated in FIGS. 6A and 6B.

In the embodiments of FIGS. 6A and 6B, six electrodes 634 are disposed on the lead body 606 in the first set 660 in a uniform spaced apart arrangement, however, any suitable number of electrodes 634 can be provided in the first set 660 in any suitable arrangement, including but not limited to two, four, eight, ten, twelve, fourteen, sixteen, or more electrodes. In some embodiments, the distal-most electrode may be a tip electrode. In the illustrated embodiment, the electrodes of the first set 660 are spaced apart from each other by a first distance 670. It will be understood, however, that the electrode spacing in the first set 660 need not be uniform. In at least some embodiments, if the first distance is not uniform between all of the electrodes of the first set, the distance comparisons describe below with respect to the second and third distances will apply to all of the first distances.

In the embodiments of FIGS. 6A and 6B, two electrodes 634 are disposed on the lead body 606 in the second set 662 in a uniform spaced apart arrangement, however, any suitable number of electrodes 634 can be provided in any suitable arrangement, including but not limited to two, three, four, six, eight, ten, twelve, fourteen, sixteen, or more electrodes. In the illustrated embodiment, the electrodes of the second set 662 are spaced apart from each other by a second distance 672. It will be understood, however, that the electrode spacing in the second set 662 need not be uniform. In at least some embodiments, if the second distance is not uniform between all of the electrodes of the second set, the distance comparisons describe below with respect to the first and third distances will apply to all of the second distances. In some alternative embodiments, the second set includes a single electrode and, therefore, such embodiments do not have a second distance.

The first set 660 is spaced apart from the second set 662 by a third distance 674. The second distance 672 is greater than the first distance 670. The third distance is equal to (FIG. 6A) or greater than (FIG. 6B) that the second distance 672. In at least some embodiments, the third distance 674 is at least twice the second distance 672, as illustrated in FIG. 6B. In at least some embodiments, the third distance 674 is at least twice the first distance 672, as illustrated in both FIGS. 6A and 6B, and the third distance 674 can be at least four, five, six, eight, ten, twelve, fourteen, or more times the first distance 672 (see, FIG. 6B). In FIG. 6B, the electrodes of the first set 660 are spaced closer together than those in the embodiment illustrated in FIG. 6A.

The first, second, and third distances may be selected by any suitable method. For example, one or more of the first, second, and third distances may be selected based on the particular anatomy of the patient and the place where the lead is to be implanted. In other embodiments, one or more of the first, second, and third distances may be selected based on the anatomy of the average adult human, average adult male, average adult female, average child, or any other group or subgroup of potential patients, or any other similar criteria. In some embodiments, one or more of the first, second, and third distances are selected based on an anticipated implantation or stimulation site. In other embodiments, one or more of the first, second, or third distances may be selected to be useful for a range of implantation or stimulation sites.

The following are examples of possible sizes and spacings for the elements of the lead. It will be understood that these are only examples and that leads with elements having other sizes and spacings are suitable. In these examples, the electrodes 634 have a longitudinal length in the range of 1 to 5 mm including, for example, in the range of 2 to 4 mm. The first distance 670 is in the range of 0.5 to 4 mm including, for example, 2.5 mm (FIG. 6A) or 1 mm (FIG. 6B). The second distance 672 is in the range of 4 to 10 mm including, for example, in the range of 5 to 7 mm. The third distance 674 is in the range of 4 to 20 mm or in the range of 6 to 16 mm including, for example, in the range of 5 to 7 mm (FIG. 6A) or in the range of 12 to 16 mm (FIG. 6B).

One or more anchoring units 650 are mounted on the lead body 606. In the illustrated embodiments of FIGS. 6A and 6B, one or more of the anchoring units 650 are mounted between the electrodes 634 of the second set 662. Optionally, one or more of the anchoring units are mounted in the space (identified by distance 674) between the first set 660 and the second set 662. It will be understood that other embodiments may include additional anchoring units being mounted elsewhere along the lead.

The anchoring units 650 may be any of the anchoring units describe above including the anchoring units 350, 450, and 550 of FIGS. 3, 4, and 5, respectively or any of the anchoring units found in U.S. Patent Application Publication No. 2010/0256696 or any other suitable anchoring units. In the embodiment shown in FIGS. 6A and 6B, four anchoring units 650 are disposed over the lead body 606; however, any suitable number of anchoring units 650 may be used including two, three, four, five, six, seven, eight, nine, ten, or more anchoring units. The anchoring units may be all the same or there may be anchoring units of two or more different types (as examples, a combination of anchoring units 350 and anchoring units 450 or a combination of anchoring units 350 and anchoring units 550 or a combination of anchoring units 550 and anchoring units 450.) The anchoring units 650 can overlap with each other or can be spaced apart from each other (as illustrated in FIGS. 6A and 6B).

Figure 6C:
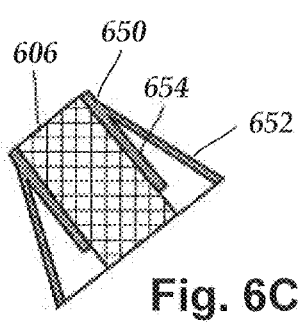
FIG. 6C is a schematic cross-sectional view of a portion of the lead body and one of the lead anchoring units of FIG. 6A, according to the invention.

FIG. 6C is a cross-sectional view of a portion of the lead body 606 and one anchoring unit 650. The anchoring unit 650 of FIG. 6C includes an anchoring element 652 and a lead attachment element 654. The lead attachment element 654 has a tubular (e.g., cylindrical) configuration defining a central attachment lumen that receives a portion of the lead body 606. The anchoring element 652 includes a cone 652 that extends over the lead attachment element 654. The cone 652 is longer than the lead attachment element 654, so that the cone extends radially over and beyond the lead attachment element 654. The radially extending cone anchors the lead to the surrounding tissue.

A variety of methods may be employed to attach the anchoring unit 650 to the lead body 606. For example, each individual anchoring unit 650 can be slid onto the lead body 606 to the desired position along the lead body. In some embodiments, the anchoring unit 650 is swelled prior to sliding on the lead body. As an example, a silicone anchoring unit 650 can be treated with a heptane solution to swell the anchoring unit so that it can be slid onto the lead body. As the heptane evaporates, the anchoring unit 650 will return to its original dimensions. In some embodiments, a portion of the lead body 606 where the anchoring unit 650 is to be placed may be ablated to reduce the diameter of the lead body at that position. In some embodiments, biocompatible adhesive may be used to attach, or enhance attachment, of the anchoring unit 650 to the lead body 606. Such adhesive may be applied prior to, or after, sliding the anchoring unit 650 onto the lead body 606.

Figure 7:
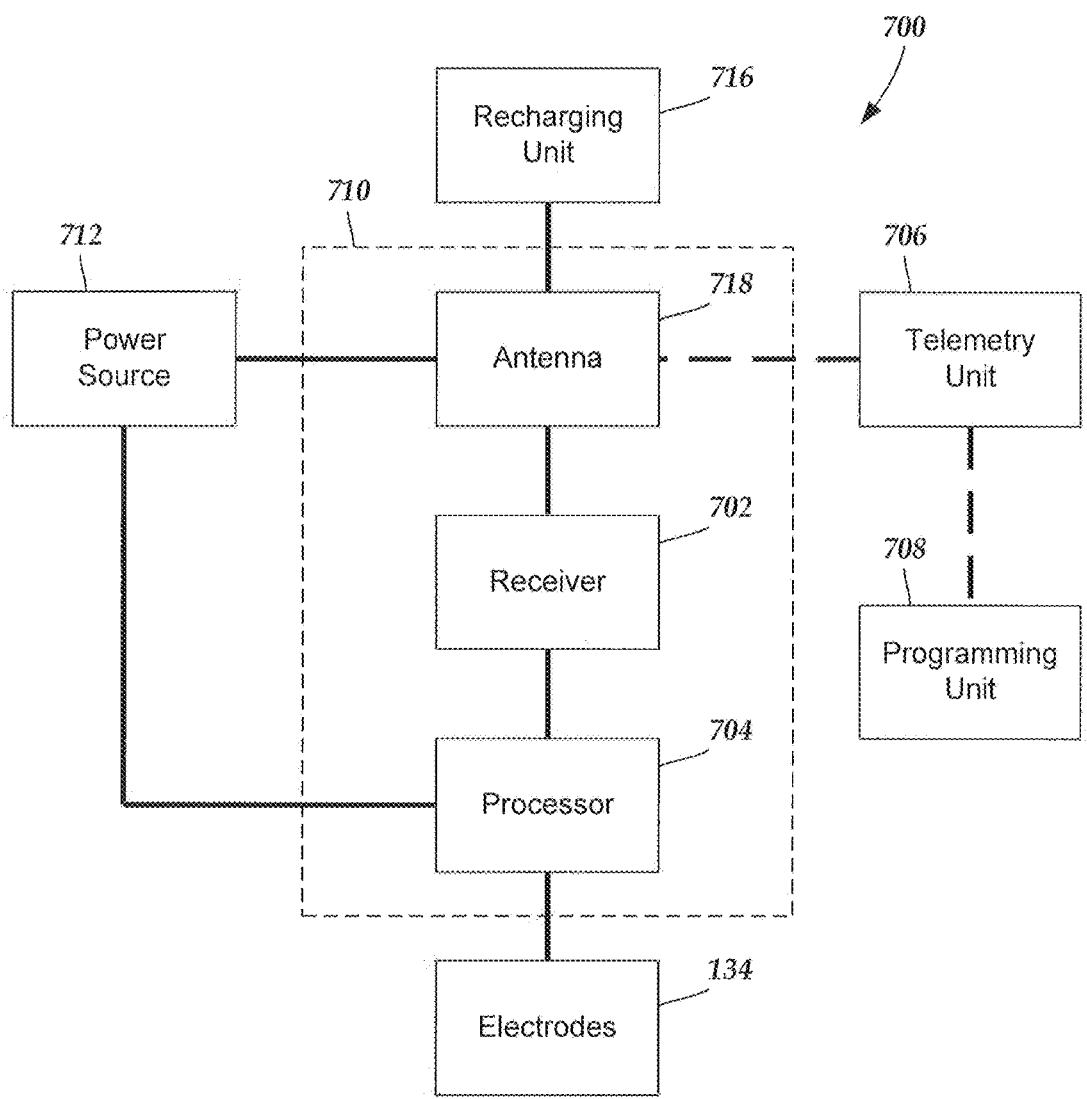
FIG. 7 is a schematic overview of one embodiment of components of a stimulation system, including an electronic subassembly disposed within a control module, according to the invention.

FIG. 7 is a schematic overview of one embodiment of components of an electrical stimulation system 700 including an electronic subassembly 710 disposed within a control module. It will be understood that the electrical stimulation system can include more, fewer, or different components and can have a variety of different configurations including those configurations disclosed in the stimulator references cited herein.

Some of the components (for example, a power source 712, an antenna 718, a receiver 702, and a processor 704) of the electrical stimulation system can be positioned on one or more circuit boards or similar carriers within a sealed housing of an implantable pulse generator, if desired. Any power source 712 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 718 or a secondary antenna. The external power source can be in a device that is mounted on the skin of the user or in a unit that is provided near the user on a permanent or periodic basis.

If the power source 712 is a rechargeable battery, the battery may be recharged using the optional antenna 718, if desired. Power can be provided to the battery for recharging by inductively coupling the battery through the antenna to a recharging unit 716 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 704 is generally included to control the timing and electrical characteristics of the electrical stimulation system. For example, the processor 704 can, if desired, control one or more of the timing, frequency, strength, duration, and waveform of the pulses. In addition, the processor 704 can select which electrodes can be used to provide stimulation, if desired. In some embodiments, the processor 704 selects which electrode(s) are cathodes and which electrode(s) are anodes. In some embodiments, the processor 704 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 708 that, for example, allows modification of pulse characteristics. In the illustrated embodiment, the processor 704 is coupled to a receiver 702 which, in turn, is coupled to the optional antenna 718. This allows the processor 704 to receive instructions from an external source to, for example, direct the pulse characteristics and the selection of electrodes, if desired.

In one embodiment, the antenna 718 is capable of receiving signals (e.g., RF signals) from an external telemetry unit 706 which is programmed by the programming unit 708. The programming unit 708 can be external to, or part of, the telemetry unit 706. The telemetry unit 706 can be a device that is worn on the skin of the user or can be carried by the user and can have a form similar to a pager, cellular phone, or remote control, if desired. As another alternative, the telemetry unit 706 may not be worn or carried by the user but may only be available at a home station or at a clinician's office. The programming unit 708 can be any unit that can provide information to the telemetry unit 706 for transmission to the electrical stimulation system 700. The programming unit 708 can be part of the telemetry unit 706 or can provide signals or information to the telemetry unit 706 via a wireless or wired connection. One example of a suitable programming unit is a computer operated by the user or clinician to send signals to the telemetry unit 706.

The signals sent to the processor 704 via the antenna 718 and the receiver 702 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 700 to cease operation, to start operation, to start charging the battery, or to stop charging the battery. In other embodiments, the stimulation system does not include the antenna 718 or receiver 702 and the processor 704 operates as programmed.

Optionally, the electrical stimulation system 700 may include a transmitter (not shown) coupled to the processor 704 and the antenna 718 for transmitting signals back to the telemetry unit 706 or another unit capable of receiving the signals. For example, the electrical stimulation system 700 may transmit signals indicating whether the electrical stimulation system 700 is operating properly or not or indicating when the battery needs to be charged or the level of charge remaining in the battery. The processor 704 may also be capable of transmitting information about the pulse characteristics so that a user or clinician can determine or verify the characteristics.

The above specification and examples provide a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation lead, comprising:
    a lead body having a distal end portion, a proximal end portion, and a longitudinal length;
    a plurality of electrodes disposed along the distal end portion of the lead body, wherein the plurality of electrodes comprises at least six electrodes, wherein all of the electrodes of the lead are divided into a first set of electrodes and a second set of electrodes adjacent to the first set of electrodes, wherein the first set of electrodes comprises at least four of the electrodes and the second set of electrodes comprises at least two of the electrodes, wherein adjacent electrodes of the first set are longitudinally spaced apart from each other by a first distance and adjacent electrodes of the second set are longitudinally spaced apart from each other by a second distance that is greater than the first distance and the first set is longitudinally spaced apart from the second set by a third distance, defined as a distance between one electrode of each of the first and second sets that are closest to each other, that is greater than or equal to the second distance;
    a plurality of terminals disposed along the proximal end portion of the lead body;
    a plurality of conductors electrically coupling the terminals to the electrodes; and
    a plurality of anchoring units disposed along the distal end portion of the lead body and proximal to all of the electrodes of the first set of electrodes, wherein at least two of the anchoring units are disposed between the first set of electrodes and the second set of electrodes and longitudinally spaced apart from each other.

2. The electrical stimulation lead of claim 1, wherein the plurality of anchoring units comprises a first set of anchoring units disposed between the first set of electrodes and the second set of electrodes and a second set of anchoring units disposed between the electrodes of the second set of electrodes.

3. The electrical stimulation lead of claim 1, wherein the second distance is at least twice the first distance.

4. The electrical stimulation lead of claim 1, wherein the third distance is at least twice the second distance.

5. The electrical stimulation lead of claim 1, wherein the third distance is equal to the second distance.

6. The electrical stimulation lead of claim 1, wherein at least one of the electrodes of the second set is proximal to all of the anchoring units.

7. The electrical stimulation lead of claim 1, wherein lead is configured and arranged for stimulation of a sacral nerve of an average adult human with the plurality of electrodes being positioned along the lead so that when the lead is implanted with the first set of electrodes near the sacral nerve for stimulation of the sacral nerve, the second set of electrodes is be positioned near the sacral foramen and the plurality of anchoring units are positioned to anchor against or proximate to the sacral foramen or fascia proximate the sacral foramen.

8. The electrical stimulation lead of claim 1, wherein the second set contains exactly two electrodes.

9. The electrical stimulation lead of claim 1, wherein at least one of the plurality of anchoring elements is disposed between adjacent electrodes of the second set of electrodes.

10. The electrical stimulation lead of claim 1, where at least one of the anchoring elements comprises a cone.

11. The electrical stimulation lead of claim 1, where at least one of the anchoring elements comprises a lead attachment element and a plurality of fins, each fin attached to, and extending away from, the lead attachment element.

12. An electrical stimulating system comprising:
the electrical stimulation lead of claim 1;
a control module coupleable to the electrical stimulation lead, the control module comprising
a housing, and
an electronic subassembly disposed in the housing; and
a connector for receiving the electrical stimulation lead, the connector having a proximal end, a distal end, and a longitudinal length, the connector comprising
a connector housing defining a port at the distal end of the connector, the port configured and arranged for receiving the proximal end portion of the lead body of the electrical stimulation lead, and
a plurality of connector contacts disposed in the connector housing, the plurality of connector contacts configured and arranged to couple to at least one of the plurality of terminals disposed on the proximal end portion of the lead body of the electrical stimulation lead.

13. The electrical stimulation system of claim 12, further comprising a lead extension coupleable to both the electrical stimulation lead and the control module.

14. An electrical stimulation lead, comprising:
a lead body having a distal end portion, a proximal end portion, and a longitudinal length;
a plurality of electrodes disposed along the distal end portion of the lead body, wherein the plurality of electrodes comprises at least six electrodes, wherein all of the electrodes of the lead are divided into a first set of electrodes and a second set of electrodes adjacent to the first set of electrodes, wherein the first set of electrodes comprises at least four of the electrodes and the second set of electrodes comprises at least two of the electrodes, wherein adjacent electrodes of the first set are longitudinally spaced apart from each other by a first distance and adjacent electrodes of the second set are longitudinally spaced apart from each other by a second distance that is greater than the first distance and the first set is longitudinally spaced apart from the second set by a third distance, defined as a distance between one electrode of each of the first and second sets that are closest to each other, that is greater than or equal to the second distance;
a plurality of terminals disposed along the proximal end portion of the lead body;
a plurality of conductors electrically coupling the terminals to the electrodes; and
a plurality of anchoring units disposed along the distal end portion of the lead body, wherein the plurality of anchoring units comprises a first set of anchoring units disposed between the first set of electrodes and the second set of electrodes and a second set of anchoring units disposed between the electrodes of the second set of electrodes, wherein each of the first and second sets of anchoring units comprises at least two anchoring units longitudinally spaced apart from each other.

15. The electrical stimulation lead of claim 14, wherein the third distance is at least twice the second distance.

16. The electrical stimulation lead of claim 14, wherein the third distance is equal to the second distance.

17. The electrical stimulation lead of claim 14, wherein at least one of the electrodes of the second set is proximal to all of the anchoring units.

18. The electrical stimulation lead of claim 14, wherein lead is configured and arranged for stimulation of a sacral nerve of an average adult human with the plurality of electrodes being positioned along the lead so that when the lead is implanted with the first set of electrodes near the sacral nerve for stimulation of the sacral nerve, the second set of electrodes is be positioned near the sacral foramen and the plurality of anchoring units are positioned to anchor against or proximate to the sacral foramen or fascia proximate the sacral foramen.

19. An electrical stimulating system comprising:
the electrical stimulation lead of claim 14;
a control module coupleable to the electrical stimulation lead, the control module comprising
a housing, and
an electronic subassembly disposed in the housing; and
a connector for receiving the electrical stimulation lead, the connector having a proximal end, a distal end, and a longitudinal length, the connector comprising
a connector housing defining a port at the distal end of the connector, the port configured and arranged for receiving the proximal end portion of the lead body of the electrical stimulation lead, and
a plurality of connector contacts disposed in the connector housing, the plurality of connector contacts configured and arranged to couple to at least one of the plurality of terminals disposed on the proximal end portion of the lead body of the electrical stimulation lead.

20. The electrical stimulation system of claim 19, further comprising a lead extension coupleable to both the electrical stimulation lead and the control module.

* * * * *